(12) United States Patent
Sotelo

(10) Patent No.: US 9,675,984 B1
(45) Date of Patent: Jun. 13, 2017

(54) RAPID CLEANER AND DISINFECTING SYSTEM

(71) Applicant: Jose Sotelo, Morton Grove, IL (US)

(72) Inventor: Jose Sotelo, Morton Grove, IL (US)

( * ) Notice: Subject to any disclaimer, the term of this patent is extended or adjusted under 35 U.S.C. 154(b) by 0 days.

(21) Appl. No.: 14/860,190

(22) Filed: Sep. 21, 2015

Related U.S. Application Data

(60) Provisional application No. 62/056,185, filed on Sep. 26, 2014.

(51) Int. Cl.
| | |
|---|---|
| *B05B 9/00* | (2006.01) |
| *B05B 9/04* | (2006.01) |
| *B08B 3/02* | (2006.01) |
| *B08B 1/04* | (2006.01) |
| *B08B 1/00* | (2006.01) |
| *B08B 7/00* | (2006.01) |
| *B08B 13/00* | (2006.01) |
| *B62B 3/10* | (2006.01) |

(52) U.S. Cl.
CPC ............ *B05B 9/007* (2013.01); *B05B 9/0423* (2013.01); *B08B 1/002* (2013.01); *B08B 1/04* (2013.01); *B08B 3/026* (2013.01); *B08B 7/0057* (2013.01); *B08B 13/00* (2013.01); *B62B 3/10* (2013.01); *B62B 2202/50* (2013.01)

(58) Field of Classification Search
CPC ........ A01M 7/0035; B05B 7/00; B05B 9/007; B05B 9/0423; B08B 3/02; B08B 3/022; B08B 3/04
USPC ........ 239/146–147, 172, 302–304, 352, 329, 239/332, 175, 176, 588, 525, 530, 532; 4/516, 517, 518, 616, 625, 626
See application file for complete search history.

(56) References Cited

U.S. PATENT DOCUMENTS

| | | | | |
|---|---|---|---|---|
| 3,021,871 A * | 2/1962 | Rodgers | .................. | B29C 53/12 138/118 |
| 3,421,694 A * | 1/1969 | Muller | ..................... | B01J 4/008 239/124 |
| 5,567,247 A * | 10/1996 | Hawes | .................. | B05B 1/1636 134/36 |
| 5,725,322 A * | 3/1998 | Evans | .................... | B05B 7/2443 239/532 |
| 6,070,808 A | 6/2000 | Kildow | | |
| 6,179,224 B1 * | 1/2001 | Huesken | .................. | A47L 13/26 239/152 |
| 6,446,881 B1 * | 9/2002 | You | ......................... | B60S 3/044 239/146 |
| 2006/0266853 A1 * | 11/2006 | Gamble, II | .......... | A01C 15/006 239/661 |
| 2008/0061166 A1 * | 3/2008 | Jacques | ............... | A01M 7/0046 239/373 |

(Continued)

*Primary Examiner* — Arthur O Hall
*Assistant Examiner* — Tuongminh Pham
(74) *Attorney, Agent, or Firm* — RG Patent Consulting; Rachel Gilboy

(57) ABSTRACT

The rapid cleaner and disinfecting system is a wheeled cart that houses two containers having a first and a second cleaning fluid that can be sprayed through one of multiple self-coiling hoses with cleaning wands attached to each hose. The distal ends of the cleaning wands are coupleable to one cleaning tool of a set of cleaning tools that are usable with one of the cleaning fluids at a time pressure sprayed through the cleaning tools. The user grips the pistol grip handle of one of the cleaning wands having a cleaning tool attached and scoures the appurtenance with the tool while being assisted with the pressure spray.

15 Claims, 5 Drawing Sheets

(56) References Cited

U.S. PATENT DOCUMENTS

| | | | |
|---|---|---|---|
| 2008/0178412 A1* | 7/2008 | Kiter | A61L 2/10 |
| | | | 15/309.2 |
| 2009/0065607 A1* | 3/2009 | Gardner | F16L 37/248 |
| | | | 239/127 |
| 2009/0148342 A1* | 6/2009 | Bromberg | A01N 59/00 |
| | | | 422/37 |
| 2012/0312390 A1 | 12/2012 | Olson et al. | |
| 2013/0133702 A1 | 5/2013 | Reid | |

* cited by examiner

RAPID CLEANER AND DISINFECTING SYSTEM

CROSS-REFERENCE TO RELATED APPLICATION

The present application is related to and claims priority from prior provisional application Ser. No. 62/056,185, filed Sep. 26, 2014 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of janitorial cleaning machines and more specifically relates to power-driven cleaning machine for use with a formulated disinfecting agent.

2. Description of the Related Art

For the majority of Americans, household chores are a fact of life. Chores such as cleaning and taking out the garbage are necessary to be able to remain living in the same location for very long. If chores are neglected long enough, the end result is much more expensive than if they had been performed all along. Frequent chores are also necessary in order to make a home or place of business presentable to friends or customers. When the necessary chores of cleaning are continually neglected, an individual tends to not have many friends and a business tends to lose its customers. There is however, a secondary reason for cleaning. As our modern societies become more advanced, travel becomes more available to the citizens of other countries, and diseases that were never known before in this country become more commonplace. The cost of healthcare in this country is high and disease from the lack of cleanliness is avoidable. Many families understand the importance of cleanliness and the vast majority of business people understand the negative impact on business when cleanliness is neglected. With large amounts of traffic going through these establishments every day, most of them have to employ a full time janitorial staff in order to maintain cleanliness in each portion of the building. In both homes and particularly public accommodations, keeping a clean bathroom is of the utmost concern.

The one room in the home where people shower or bathe, brush their teeth, shave, apply make-up and undergo other personal grooming tasks; the bathroom is continuously accessed throughout the day by family members and guests. Additionally, the bathroom houses that most necessary of items: the toilet. Because so much time is spent in the bathroom, conscientious people undergo simple steps to ensure a healthy and clean bathroom environment. Regularly scrubbing the toilet bowl, scouring the sink, and washing the floor can help reduce the spread of germs and bacteria in the bathroom and can facilitate a pleasant, sanitary atmosphere. Hospitals, medical establishments, and restaurants especially are under the microscope. It is very unappetizing to go the washroom in a restaurant and find it filthy. It raises questions about the safety of the kitchen environment. It would be a contradiction to have filthy bathrooms in a hospital environment where people are supposed to be getting healed. Both household and professional cleaners would attest that completely cleaning a bathroom is an arduous, time-consuming process, and an expensive one for businesses who have to hire janitorial staffs. Labor intensity and the cost of cleaning are two variables that can be reduced to benefit a business or an organization. An innovation that could significantly reduce these factors is needed.

Various attempts have been made to solve the above-mentioned problems such as those found in U.S. Pat. No. 6,070,808 to Richard D Kildow; U.S. Pub. No. 2012/0312390 to Mark C. Schwei; and U.S. Pat. No. 2013/0133702 to John H. Reid. This art is representative of cleaning machines. None of the above inventions and patents, taken either singly or in combination, is seen to describe the invention as claimed.

Ideally, a janitorial cleaning machine should provide power scrubbing and efficient disinfection, and yet, would operate reliably and be manufactured at a modest expense. Thus, a need exists for a reliable rapid cleaner and disinfecting system to avoid the above-mentioned problems.

BRIEF SUMMARY OF THE INVENTION

In view of the foregoing disadvantages inherent in the known janitorial cleaning machine art, the present invention provides a novel rapid cleaner and disinfecting system. The general purpose of the present invention, which will be described subsequently in greater detail, is to provide power scrubbing and efficient disinfection.

The rapid cleaner and disinfecting system preferably comprises a main body including a back wall, two opposite side walls, a bottom section including an interior bottom floor portion and a top section together forming an inner volume, a first container and a second container adapted to be removably located within the inner volume, a first cleaning fluid and a second cleaning fluid located within the first container and the second container respectively, a plurality of wheels attached to the underside of the bottom section of the main body, a push handle rigidly attached to the back wall, a front access door pivotally connected via at least one hinge to one front edge of one side wall to cover the inner volume, a plurality of flexible hoses adapted to be in communication with the first container and the second container, a plurality of cleaning wands coupled to the plurality of flexible hoses, a plurality of cleaning tools each adapted to be removably coupled to the plurality of cleaning wands, at least one positive displacement pump adapted to receive the first cleaning fluid from the first container and the second cleaning fluid from the second container, and a positive displacement pump is adapted to pump the first cleaning fluid and the second cleaning fluid to the plurality of flexible hoses to be pressure sprayed through the cleaning tools for cleaning the appurtenances of a lavatory.

The cleaning tools preferably include an adjustable spray nozzle, a rotary sponge, a 45 degree angled brush, and an ultraviolet light. The positive displacement pump is adapted to provide approximately 500 psi at the tip of the cleaning wands that are attached to the flexible hoses. The rapid cleaner and disinfecting system further may include a plurality of valves connected to a manifold that is mounted to the interior surface of the main body and that is coupled to the first container and the second container such that cleaning fluids are received by the positive displacement pump from the containers and pumped through the manifold to the flexible hoses. The valves are conveniently accessible from the exterior of the main body to route pressurized spray through whichever flexible hose the user prefers. Each valve is able to control the flow volume of the first and second cleaning fluids as they are pumped through the flexible hoses to the cleaning wands. In a preferred embodiment, the flexible hoses are each self-coiling to allow extra reach while keeping the hoses neat and untangled. The rapid cleaner and disinfecting system further includes a plurality of wand holders fastened to one of the side walls. The cleaning wands are adapted to function as a pistol grip style handle for the plurality of cleaning tools. The cleaning wand holders are positioned to hold the cleaning wands vertically in a parallel planar arrangement along one side of the main body with the pistol grip style handles located near the top edge of the side wall for a convenient reaching distance by the user. The cleaning wands each have a spring loaded trigger for activating a pressure spray when the trigger is depressed, and alternately for ceasing the pressure spray when the trigger is released. The cleaning wands may be of different lengths for versatility of use and have an 8 inch extension, two twelve inch extensions, a 12 inch extension having a 90 degree bend at the distal end, and a 30 inch extension. The 30 inch extension is adapted to couple to the rotary sponge at a distal end of the 30 inch extension. The cleaning tools are coupleable to the distal end of each of the cleaning wands and may be interchangeable between the different wands.

The main body is approximately 32 inches in height and approximately 18 inches in width and sets upon a plurality of wheels that are each independently operable from each other. The top section of the main body further includes two access doors hinged on the rearmost side to open upwardly for accessing a first fill spout for the first container and a second fill spout for the second container. The first and second containers are each rectangular in shape and are positioned beside each other when installed within the inner volume of the main body. The first container is adapted to contain approximately 3 gallons of the first cleaning fluid and the second container is adapted to contain approximately 1 gallon of the second cleaning fluid. The first cleaning fluid comprises approximately 3 parts of water to approximately 1 part of Chlorine. The second cleaning fluid comprises a composition of vinegar, liquid detergent, water, lemon juice, and baking soda.

The rapid cleaner and disinfecting system further may include an air compressor for combining pressurized air with the first and second cleaning fluids to increase the scouring action of the cleaning tools. The compressed air enters the piping in the manifold downstream of a check valve that prevents compressed air from entering the pump or the containers. An adjustable pressure switch maintains a predetermined pressure to prevent over pressurization of the system. In practical operation, when a trigger of one of the pistol grips is depressed, the positive displacement pump and the compressor are activated. When the trigger is released, the flow is blocked in the pistol grip allowing the pressure to build to the set point and then the pump and the compressor are deactivated.

The adjustable spray nozzle preferably allows the spray to be adjusted from a sharp stream to a fan or cone shaped spray with the spray pressure and volume being adjusted by the corresponding valve located just above the wand holder for that wand. The rotary sponge may become operational via the fluid pressure reaching the distal end of the wand turning the sponge through the use of a turbine-like structure, or it may be activated by an electric motor. The revolutions per minute may be variable depending on the volume and pressure of cleaning fluid passing through the wand. The 45 degree angled brush may be stationary at the distal end of a wand or may oscillate, rotate, vibrate, or have some other such motion to reduce labor intensity. The ultra violet light is a cleaning tool that is attached to the distal end of one cleaning wand that is used as a secondary disinfection device for lavatory fixtures and appurtenances.

The rapid cleaner and disinfecting system may be sold completely assembled or may be sold in a kit for the user to assemble. A kit for the rapid cleaner and disinfecting system may include: a housing; a push handle; a set of wheels with fasteners; a first and a second container; a positive displacement pump; a compressor; a manifold; a set of self coiling hoses; a set of cleaning wands; a set of cleaning tools; and a volume of a first cleaning fluid and a second cleaning fluid A method of using the rapid cleaner and disinfecting system may include: filling a first container and a second container with a first cleaning fluid and a second cleaning fluid respectively; rolling the rapid cleaner and disinfecting system to the location to be used; plugging the rapid cleaner and disinfecting system to a power source; unsnapping the preferred cleaning wand(s) with the preferred cleaning tools from the corresponding wand holders; using the rapid cleaner and disinfecting system; and storing the rapid cleaner and disinfecting system.

The present invention holds significant improvements and serves as a rapid cleaner and disinfecting system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, rapid cleaner and disinfecting system, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a janitorial cleaning machine and more particularly to a rapid cleaner and disinfecting system as used to improve the ease and efficiency of cleaning bathroom appurtenances.

Generally speaking, rapid cleaner and disinfecting system is a wheeled cart that houses two containers having a first and a second cleaning fluid that can be sprayed through one of multiple self-coiling hoses with cleaning wands attached to each hose. The distal ends of the cleaning wands are coupleable to one cleaning tool of a set of cleaning tools that are usable with one of the cleaning fluids and pressure sprayed through the cleaning tools. The user grips the pistol grip handle of one of the cleaning wands having a cleaning tool attached and scours the appurtenance with the tool while being assisted with the pressure spray.

Figure 1:
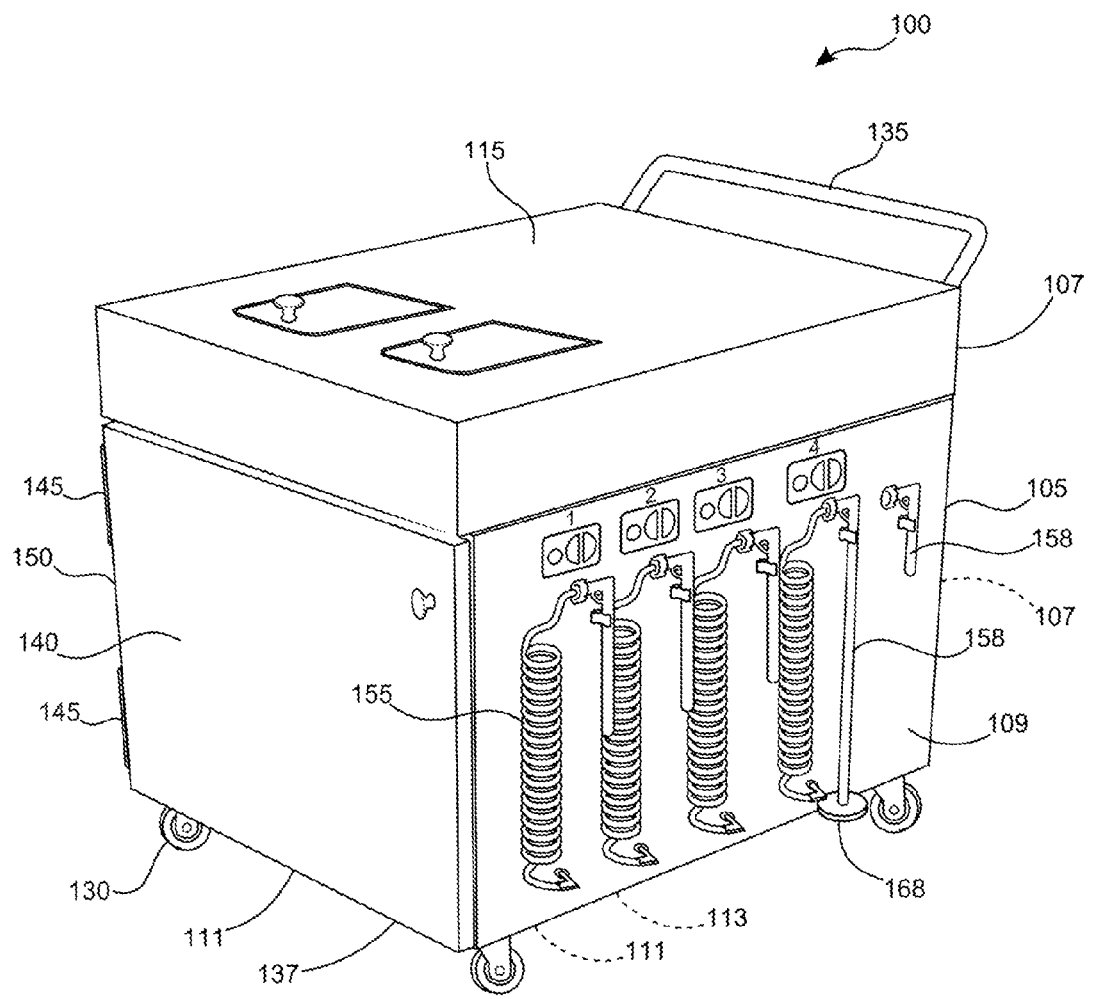
FIG. 1 shows a perspective view illustrating a rapid cleaner and disinfecting system according to an embodiment of the present invention.

Referring to the drawings by numerals of reference there is shown in FIG. 1, a perspective view illustrating rapid cleaner and disinfecting system 100 according to an embodiment of the present invention.

Rapid cleaner and disinfecting system 100 preferably comprises main body 105 including back wall 107, two opposite side wall(s) 109, bottom section 111 including interior bottom floor portion 113 and top section 115 together forming inner volume 117, first container 120 and second container 125 adapted to be removably located within inner volume 117, first cleaning fluid 122 and second cleaning fluid 127 located within first container 120 and second container 125 respectively, a plurality of wheel(s) 130 attached to underside 137 of bottom section 111 of main body 105, push handle 135 rigidly attached to back wall 107, front access door 140 pivotally connected via at least one hinge 145 to one front edge 150 of one side wall(s) 109 to cover inner volume 117, a plurality of flexible hoses 155 adapted to be in communication with first container 120 and second container 125, a plurality of cleaning wands 158 coupled to the plurality of cleaning wands 158, a plurality of cleaning tools 168 each adapted to be removably coupled to the plurality of cleaning wands 158, at least one positive displacement pump 170 adapted to receive the first cleaning fluid 122 from the first container 120 and the second cleaning fluid 127 from the second container 125, and a positive displacement pump 170 is adapted to pump first cleaning fluid 122 and second cleaning fluid 127 to the plurality of flexible hoses 155 to be pressure sprayed through cleaning tools 168 for cleaning the appurtenances of a lavatory.

Figure 2:
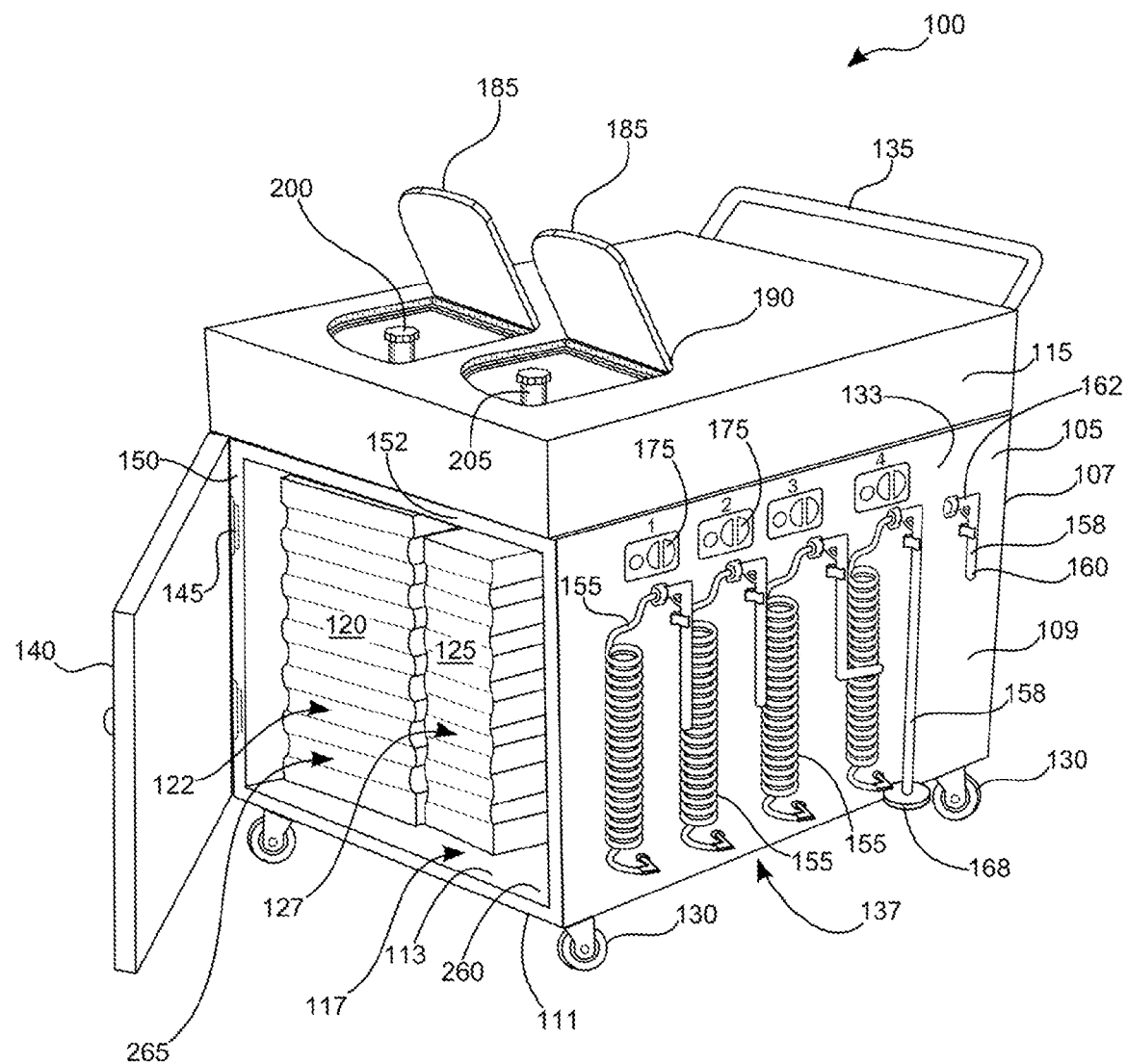
FIG. 2 is a perspective view illustrating a rapid cleaner and disinfecting system according to an embodiment of the present invention of FIG. 1.

Referring now to FIG. 2, a perspective view illustrating rapid cleaner and disinfecting system 100 according to an embodiment of the present invention of FIG. 1.

Main body 105 is approximately 32 inches in height and approximately 18 inches in width and sets upon a plurality of wheel(s) 130 that are each independently operable from each other. Top section 115 of main body 105 further includes two access doors 185 hinged on the rearmost side to open upwardly for accessing first fill spout 200 for first container 120 and second fill spout 205 for second container 125. First 120 and second container 125 are each rectangular in shape and are positioned beside each other when installed within inner volume 117 of main body 105. First container 120 is adapted to contain approximately 3 gallons of first cleaning fluid 122 and second container 125 is adapted to contain approximately 1 gallon of second cleaning fluid 127. First cleaning fluid 122 comprises approximately 3 parts of water to approximately 1 part of chlorine. Second cleaning fluid 127 comprises a composition of vinegar, liquid detergent, water, lemon juice, and baking soda.

Figure 3:
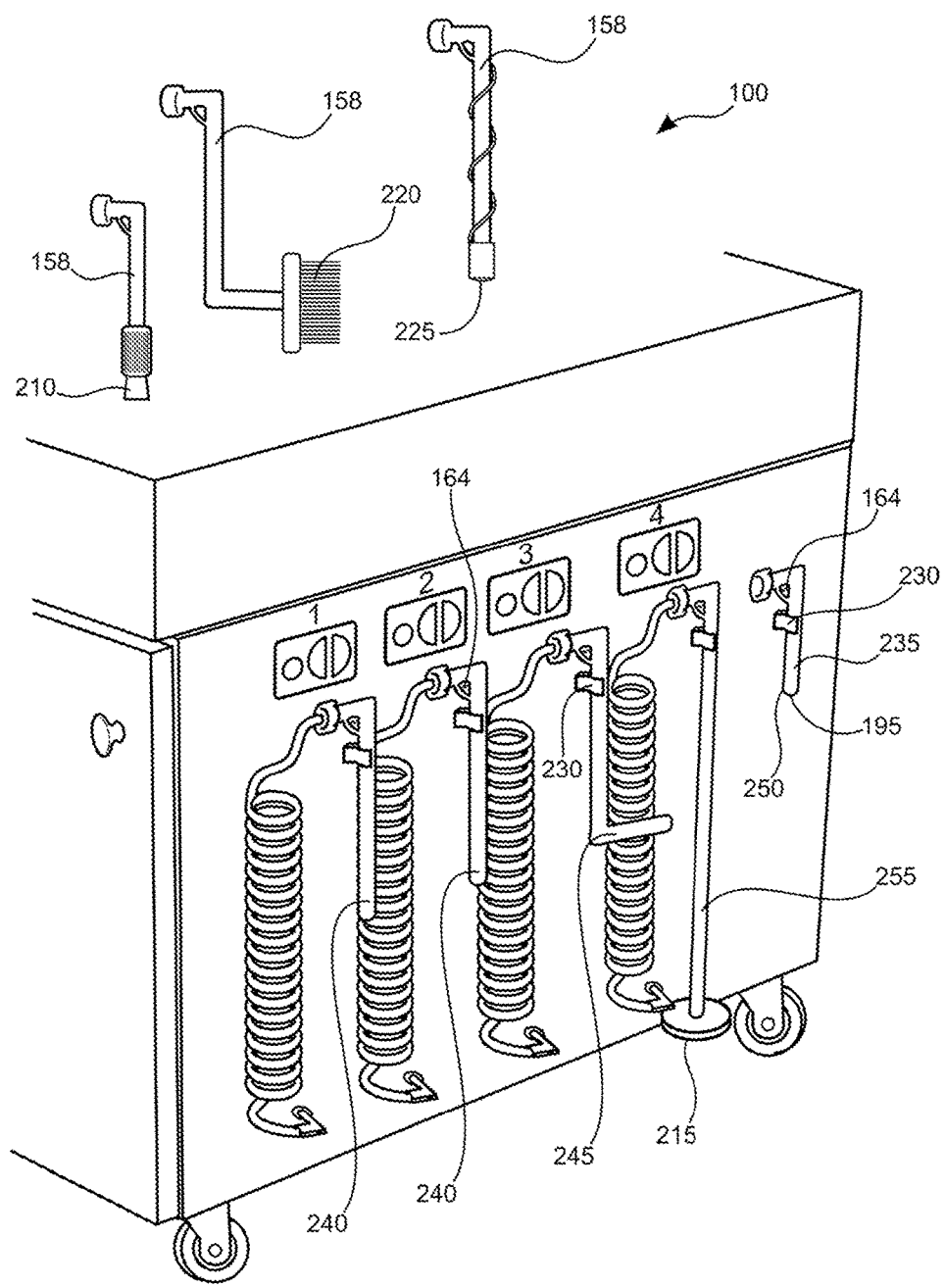
FIG. 3 is a perspective view illustrating the flexible hoses and wands of the rapid cleaner and disinfecting system according to an embodiment of the present invention of FIG. 1.

Referring now to FIG. 3, a perspective view illustrating flexible hoses 155 and cleaning wands 158 of rapid cleaner and disinfecting system 100 according to an embodiment of the present invention of FIG. 1.

Rapid cleaner and disinfecting system 100 further includes a plurality of wand holders 230 fastened to one of side wall(s) 109. Cleaning wands 158 are adapted to function as pistol grip style handle 162 for the plurality of cleaning tools 168. Wand holders 230 are positioned to hold the cleaning wands 158 vertically in a parallel planar arrangement along one side of main body 105 with pistol grip style handle 162 located near top edge 152 of the side wall(s) 109 for a convenient reaching distance by the user. Cleaning wands 158 each have spring loaded trigger 164 for activating a pressure spray when spring loaded trigger 164 is depressed, and alternately for ceasing the pressure spray when spring loaded trigger 164 is released. Cleaning wands 158 may be of different lengths for versatility of use and have an 8 inch extension, two twelve inch extensions 240, 12 inch extension 240 having a 90 degree bend 245 at distal end 250, and 30 inch extension 255. 30 inch extension 255 is adapted to couple to rotary sponge 215 at distal end 250 of 30 inch extension 255. Cleaning tools 168 are coupleable to distal end 160 of each of cleaning wands 158 and may be interchangeable between the different cleaning wands 158. Positive displacement pump 170 is adapted to provide approximately 500 psi at the tip of cleaning wands 158 that are attached to flexible hoses 155. Cleaning tools 168 preferably include an adjustable spray nozzle 210, rotary sponge 215, 45 degree angled brush 220, and ultraviolet light 225.

Adjustable spray nozzle 210 preferably allows the spray to be adjusted from a sharp stream to a fan or cone shaped spray with the spray pressure and volume being adjusted by the corresponding valve(s) 175 located just above wand holder(s) 230 for that cleaning wand 158. Rotary sponge 215 may become operational via the fluid pressure reaching distal end 250 of cleaning wand(s) 158 turning rotary sponge 215 through the use of a turbine-like structure, or it may be activated by an electric motor. The revolutions per minute may be variable depending on the volume and pressure of first cleaning fluid 122 or second cleaning fluid 127 passing through cleaning wand(s) 158. 45 degree angled brush 220 may be stationary at distal end 160 of cleaning wand(s) 158 or may oscillate, rotate, vibrate, or have some other such motion to reduce labor intensity. Ultraviolet light 225 is cleaning tool(s) 168 that is attached distal end 250 of one cleaning wand(s) 158 that is used as a secondary disinfection device for lavatory fixtures and appurtenances.

Figure 4:
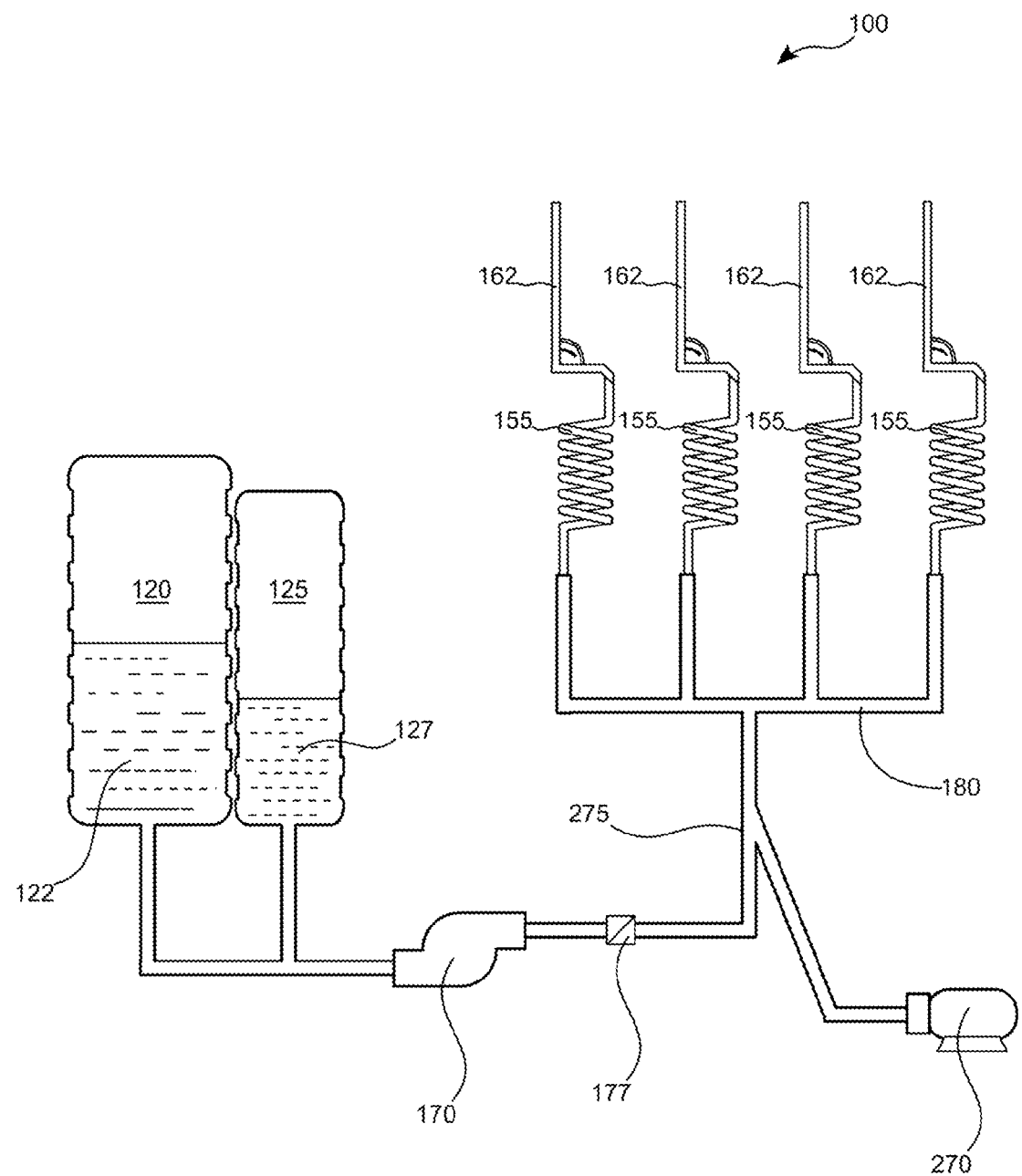
FIG. 4 is a diagram illustrating the liquid flow through the rapid cleaner and disinfecting system according to an embodiment of the present invention of FIG. 1.

Referring now to FIG. 4, showing a diagram illustrating the liquid flow through rapid cleaner and disinfecting system 100 according to an embodiment of the present invention of FIG. 1.

Rapid cleaner and disinfecting system 100 further may include a plurality of valve(s) 175 connected to manifold 180 that is mounted to interior surface 260 of main body 105 and that is coupled to first container 120 and second container 125 such that cleaning fluids 265 are received by positive displacement pump 170 from first 120 and second container 125 and pumped through manifold 180 to flexible hoses 155. Valve(s) 175 are conveniently accessible from the exterior of main body 105 to route pressurized spray through whichever flexible hose 155 the user prefers. Each valve(s) 175 is able to control the flow volume of first cleaning fluid 122 and second cleaning fluid 127 as they are pumped through flexible hoses 155 to cleaning wand(s) 158.

Rapid cleaner and disinfecting system 100 further may include air compressor 270 for combining pressurized air with first 122 and second cleaning fluid 127 to increase the scouring action of cleaning tool(s) 168. The compressed air enters the piping 275 in manifold 180 downstream of check valve 177 that prevents compressed air from entering positive displacement pump 170 or first 120 and second container 125. An adjustable pressure switch maintains a predetermined pressure to prevent over pressurization of the system. In practical operation, when spring loaded trigger 164 of one of pistol grip style handle 162 is depressed, positive displacement pump 170 and air compressor 270 are activated. When spring loaded trigger 164 is released, the flow is blocked in pistol grip style handle 162 allowing the pressure to build to the set point and then positive displacement pump 170 and air compressor 270 are deactivated.

Rapid cleaner and disinfecting system 100 may be sold as kit 450 comprising the following parts: at least one main body 105; at least one push handle 135; at least one set of wheel(s) 130 with fasteners; at least one first 120 and one second container 125; at least one positive displacement pump 170; at least one air compressor 270; at least one manifold 180; at least one set of flexible hoses 155; at least one set of cleaning wand(s) 158; at least one set of cleaning tool(s) 168; at least one volume of first cleaning fluid 122 and second cleaning fluid 127; and at least one set of user instructions. The kit has instructions such that functional relationships are detailed in relation to the structure of the invention (such that the invention can be used, maintained, or the like in a preferred manner). Rapid cleaner and disinfecting system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
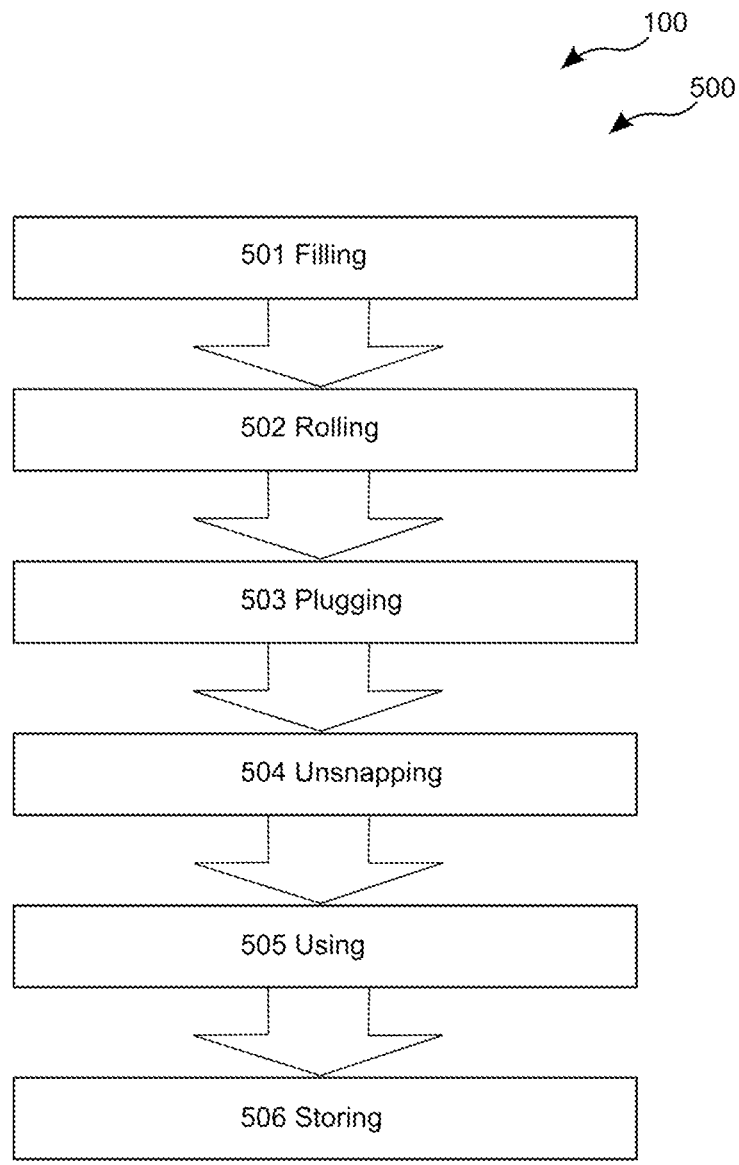
FIG. 5 is a flowchart illustrating a method of use for rapid cleaner and disinfecting system according to an embodiment of the present invention of FIGS. 1-4.

Referring now to FIG. 5, showing method of use 500 for rapid cleaner and disinfecting system 100. A method of using rapid cleaner and disinfecting system 100 may comprise the steps of step one 501 filling first container 120 and second container 125 with first cleaning fluid 122 and second cleaning fluid 127 respectively; step two 502 rolling rapid cleaner and disinfecting system 100 to the location to be used; step three 503 plugging rapid cleaner and disinfecting system 100 to a power source; step four 504 unsnapping the preferred cleaning wand(s) 158 with the preferred cleaning tool(s) 168 from the corresponding wand holder(s) 230; step five 505 using rapid cleaner and disinfecting system 100; and step six 506 storing rapid cleaner and disinfecting system 100.

It should be noted that step 501 is an optional step and may not be implemented in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. §112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A rapid cleaner and disinfecting system comprising:
 a main body including a back wall, two opposite side walls, a bottom section including an interior bottom floor portion, and a top section together forming an inner volume;
 a first container and a second container adapted to be removably located within said inner volume;
 a first cleaning fluid and a second cleaning fluid located within said first container and said second container respectively;
 a plurality of wheels attached to an underside of said bottom section of said main body;
 a push handle rigidly attached to said back wall;
 a front access door pivotally connected via at least one hinge to a front edge of one of said two opposite side walls to cover said inner volume;
 a plurality of flexible hoses adapted to be in communication with said first container and said second container;
 a plurality of cleaning wands coupled to said plurality of flexible hoses;
 a plurality of cleaning tools each adapted to be removably coupled to said plurality of cleaning wands;
 at least one positive displacement pump adapted to receive said first cleaning fluid from said first container and said second cleaning fluid from said second container, and wherein said at least one positive displacement pump is adapted to pump said first cleaning fluid and said second cleaning fluid to said plurality of flexible hoses to be pressure sprayed through one of said plurality of cleaning tools at a time for cleaning at least one appurtenance of a lavatory;

a plurality of valves connected to and accessible from an exterior of said main body; and a manifold connected to an interior surface of said main body and is in communication with said first container and said second container, and wherein said plurality of valves are coupled to said manifold such that each said valve is able to control a volume of said first cleaning fluid and said second cleaning fluid pumped through said flexible hoses and passing through each said cleaning wand;

wherein said first cleaning fluid comprises approximately 3 parts of water to approximately 1 part of chlorine;

wherein said second cleaning fluid comprises a composition of vinegar, liquid detergent, water, lemon juice, and baking soda; and wherein said plurality of flexible hoses are each self-coiling.

2. The rapid cleaner and disinfecting system of claim 1 wherein said main body is approximately 32 inches in height and approximately 18 inches in width.

3. The rapid cleaner and disinfecting system of claim 2 wherein said top section of said main body further comprises two access doors hinged on a rearmost side to open upwardly for accessing a first fill spout of said first container and a second fill spout of said second container.

4. The rapid cleaner and disinfecting system of claim 1 wherein said first container and said second container are each rectangular in shape and are positioned beside each other when installed within said inner volume of said main body.

5. The rapid cleaner and disinfecting system of claim 4 wherein said first container is adapted to contain approximately 3 gallons of said first cleaning fluid and said second container is adapted to contain approximately 1 gallon of said second cleaning fluid.

6. The rapid cleaner and disinfecting system of claim 1 wherein said rapid cleaner and disinfecting system further comprises an air compressor for combining a pressurized air with said first cleaning fluid and said second cleaning fluid to cause an increased scouring action and an increased cleaning efficiency of said plurality of cleaning tools.

7. The rapid cleaner and disinfecting system of claim 1 wherein said plurality of cleaning wands are adapted to function as a pistol grip style handle for said plurality of cleaning tools.

8. The rapid cleaner and disinfecting system of claim 7 wherein said plurality of cleaning wands each further comprise a spring loaded trigger for activating a pressure spray when said trigger is depressed, and alternately for ceasing a pressure spray when said trigger is released.

9. The rapid cleaner and disinfecting system of claim 7 wherein said plurality of cleaning tools are coupleable to a distal end of each of said plurality of cleaning wands.

10. The rapid cleaner and disinfecting system of claim 1 wherein said at least one positive displacement pump is adapted to provide approximately 500 psi at a wand tip of each said cleaning wands.

11. The rapid cleaner and disinfecting system of claim 7 wherein said plurality of cleaning tools comprise an adjustable spray nozzle, a rotary sponge, a 45 degree angled brush, and an ultraviolet light.

12. The rapid cleaner and disinfecting system of claim 7 wherein said plurality of cleaning wands include an 8 inch extension, two twelve inch extensions, a 12 inch extension having a 90 degree bend at a distal end, and a 30 inch extension.

13. The rapid cleaner and disinfecting system of claim 12 wherein said 30 inch extension is adapted to couple to a rotary sponge at a distal end of said 30 inch extension.

14. The rapid cleaner and disinfecting system of claim 1 wherein said plurality of wheels are each independently operable from each other.

15. The rapid cleaner and disinfecting system of claim 1 wherein said rapid cleaner and disinfecting system further comprises a plurality of wand holders fastened to one of said side walls.

* * * * *